United States Patent [19]
Kajiyama et al.

[11] Patent Number: 5,229,285
[45] Date of Patent: Jul. 20, 1993

[54] THERMOSTABLE LUCIFERASE OF FIREFLY, THERMOSTABLE LUCIFERASE GENE OF FIREFLY, NOVEL RECOMBINANT DNA, AND PROCESS FOR THE PREPARATION OF THERMOSTABLE LUCIFERASE OF FIREFLY

[75] Inventors: Naoki Kajiyama; Eiichi Nakano, both of Noda, Japan

[73] Assignee: Kikkoman Corporation, Japan

[21] Appl. No.: 903,047

[22] Filed: Jun. 23, 1992

[30] Foreign Application Priority Data

Jun. 27, 1991 [JP] Japan ................... 3-157117
Nov. 29, 1991 [JP] Japan ................... 3-317064
May 22, 1992 [JP] Japan ................... 4-131057

[51] Int. Cl.⁵ .................. C12N 9/02; C12N 15/53
[52] U.S. Cl. .................. 435/189; 435/69.1;
435/71.2; 435/252.3; 435/252.33; 435/320.1;
435/172.3; 435/172.1; 536/23.2; 935/9; 935/14;
935/29; 935/56; 935/72; 935/73
[58] Field of Search .................. 435/69.1, 71.2, 252.3,
435/252.33, 320.1, 172.3, 172.1; 536/23.2;
935/9, 14, 29, 56, 72, 73, 10

[56] References Cited
FOREIGN PATENT DOCUMENTS

0275202A3  7/1988  European Pat. Off. .
0318915A3  6/1989  European Pat. Off. .
0337349A3  10/1989  European Pat. Off. .
92110808  11/1992  European Pat. Off. .

OTHER PUBLICATIONS

Abstract, Ester et al., Biolumin., Chemilumin. Proc. Int. Symp., 6th Meeting Date 1990, Chichester, UK, "Engineering of a bacterial luciferase alpha-beta fusion protein with enhanced activity at 37° C. in *Escherichia coli*".

*Primary Examiner*—Robert A. Wax
*Assistant Examiner*—Rebecca Prouty
*Attorney, Agent, or Firm*—Pennie & Edmonds

[57] ABSTRACT

The present invention relates to thermostable luciferase of firefly wherein an amino acid at the 217-position of the amino acid sequence of wild-type firefly luciferase or an amino acid equivalent to the amino acid at the 217-position of luciferase of GENJI firefly or HEIKE firefly is converted into a hydrophobic amino acid, a gene encoding said thermostable luciferase, a vector comprising the gene encoding said thermostable luciferase inserted therein, and a process for the preparation of thermostable firefly luciferase comprising use of said vector.

5 Claims, 2 Drawing Sheets

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 1644 base pairs
        ( B ) TYPE: nucleic acid
        ( C ) STRANDEDNESS: single
        ( D ) TOPOLOGY: unknown     ( i i ) MOLECULE TYPE: cDNA to mRNA     ( x i ) SEQUENCE DESCRIPTION: SEQ ID NO:1:

```
ATGGAAAACA  TGGAAAACGA  TGAAAATATT  GTAGTTGGAC  CTAAACCGTT  TTACCCTATC     60
GAAGAGGGAT  CTGCTGGAAC  ACAATTACGC  AAATACATGG  AGCGATATGC  AAAACTTGGC    120
GCAATTGCTT  TTACAAATGC  AGTTACTGGT  GTTGATTATT  CTTACGCCGA  ATACTTGGAG    180
AAATCATGTT  GTCTAGGAAA  AGCTTTGCAA  AATTATGGTT  TGGTTGTTGA  TGGCAGAATT    240
GCGTTATGCA  GTGAAAACTG  TGAAGAATTT  TTTATTCCTG  TAATAGCCGG  ACTGTTTATA    300
GGTGTAGGTG  TTGCACCCAC  TAATGAGATT  TACACTTTAC  GTGAACTGGT  TCACAGTTTA    360
GGTATCTCTA  AACCAACAAT  TGTATTTAGT  TCTAAAAAAG  GCTTAGATAA  AGTTATAACA    420
GTACAGAAAA  CAGTAACTAC  TATTAAAACC  ATTGTTATAC  TAGATAGCAA  AGTTGATTAT    480
CGAGGATATC  AATGTCTGGA  CACCTTTATA  AAAAGAAACA  CTCCACCAGG  TTTTCAAGCA    540
TCCAGTTTCA  AAACTGTGGA  AGTTGACCGT  AAAGAACAAG  TTGCTCTTAT  AATGAACTCT    600
TCGGGTTCTA  CCGGTTTGCC  AAAAGGCGTA  CAACTTACTC  ACGAAAATAC  AGTCACTAGA    660
TTTTCTCATG  CTAGAGATCC  GATTTATGGT  AACCAAGTTT  CACCAGGCAC  CGCTGTTTTA    720
ACTGTCGTTC  CATTCCATCA  TGGTTTTGGT  ATGTTCACTA  CTCTAGGGTA  TTTAATTTGT    780
GGTTTTCGTG  TTGTAATGTT  AACAAAATTC  GATGAAGAAA  CATTTTTAAA  AACTCTACAA    840
GATTATAAAT  GTACAAGTGT  TATTCTTGTA  CCGACCTTGT  TTGCAATTCT  CAACAAAAGT    900
GAATTACTCA  ATAAATACGA  TTTGTCAAAT  TTAGTTGAGA  TTGCATCTGG  CGGAGCACCT    960
TTATCAAAAG  AAGTTGGTGA  AGCTGTTGCT  AGACGCTTTA  ATCTTCCCGG  TGTTCGTCAA   1020
GGTTATGGTT  TAACAGAAAC  AACATCTGCC  ATTATTATTA  CACCAGAAGG  AGACGATAAA   1080
CCAGGAGCTT  CTGGAAAAGT  CGTGCCGTTG  TTTAAAGCAA  AAGTTATTGA  TCTTGATACC   1140
AAAAAATCTT  TAGGTCCTAA  CAGACGTGGA  GAAGTTTGTG  TTAAAGGACC  TATGCTTATG   1200
AAAGGTTATG  TAAATAATCC  AGAAGCAACA  AAAGAACTTA  TTGACGAAGA  AGGTTGGCTG   1260
CACACCGGAG  ATATTGGATA  TTATGATGAA  GAAAAACATT  TCTTTATTGT  CGATCGTTTG   1320
AAGTCTTTAA  TCAAATACAA  AGGATACCAA  GTACCACCTG  CCGAATTAGA  ATCCGTTCTT   1380
```

```
TTGCAACATC CATCTATCTT TGATGCTGGT GTTGCCGGCG TTCCTGATCC TGTAGCTGGC    1440

GAGCTTCCAG GAGCCGTTGT TGTACTGGAA AGCGGAAAAA ATATGACCGA AAAAGAAGTA    1500

ATGGATTATG TTGCAAGTCA AGTTTCAAAT GCAAACGTT TACGTGGTGG TGTTCGTTTT     1560

GTGGATGAAG TACCTAAAGG TCTTACTGGA AAAATTGACG GCAGAGCAAT TAGAGAAATC    1620

CTTAAGAAAC CAGTTGCTAA GATG                                           1644
```

( 2 ) INFORMATION FOR SEQ ID NO:2:

( i ) SEQUENCE CHARACTERISTICS:
        ( A ) LENGTH: 548 amino acids
        ( B ) TYPE: amino acid
        ( C ) STRANDEDNESS: single
        ( D ) TOPOLOGY: unknown     ( i i ) MOLECULE TYPE: peptide     ( x i ) SEQUENCE DESCRIPTION: SEQ ID NO:2:

```
Met Glu Asn Met Glu Asn Asp Glu Asn Ile Val Val Gly Pro Lys Pro
 1               5                  10                  15

Phe Tyr Pro Ile Glu Glu Gly Ser Ala Gly Thr Gln Leu Arg Lys Tyr
                20                  25                  30

Met Glu Arg Tyr Ala Lys Leu Gly Ala Ile Ala Phe Thr Asn Ala Val
             35                  40                  45

Thr Gly Val Asp Tyr Ser Tyr Ala Glu Tyr Leu Glu Lys Ser Cys Cys
         50                  55                  60

Leu Gly Lys Ala Leu Gln Asn Tyr Gly Leu Val Val Asp Gly Arg Ile
 65                  70                  75                  80

Ala Leu Cys Ser Glu Asn Cys Glu Glu Phe Phe Ile Pro Val Ile Ala
                 85                  90                  95

Gly Leu Phe Ile Gly Val Gly Val Ala Pro Thr Asn Glu Ile Tyr Thr
                100                 105                 110

Leu Arg Glu Leu Val His Ser Leu Gly Ile Ser Lys Pro Thr Ile Val
             115                 120                 125

Phe Ser Ser Lys Lys Gly Leu Asp Lys Val Ile Thr Val Gln Lys Thr
    130                 135                 140

Val Thr Thr Ile Lys Thr Ile Val Ile Leu Asp Ser Lys Val Asp Tyr
145                 150                 155                 160

Arg Gly Tyr Gln Cys Leu Asp Thr Phe Ile Lys Arg Asn Thr Pro Pro
                165                 170                 175

Gly Phe Gln Ala Ser Ser Phe Lys Thr Val Glu Val Asp Arg Lys Glu
            180                 185                 190

Gln Val Ala Leu Ile Met Asn Ser Ser Gly Ser Thr Gly Leu Pro Lys
        195                 200                 205

Gly Val Gln Leu Thr His Glu Asn Thr Val Thr Arg Phe Ser His Ala
    210                 215                 220

Arg Asp Pro Ile Tyr Gly Asn Gln Val Ser Pro Gly Thr Ala Val Leu
225                 230                 235                 240

Thr Val Val Pro Phe His His Gly Phe Gly Met Phe Thr Thr Leu Gly
                245                 250                 255

Tyr Leu Ile Cys Gly Phe Arg Val Val Met Leu Thr Lys Phe Asp Glu
            260                 265                 270

Glu Thr Phe Leu Lys Thr Leu Gln Asp Tyr Lys Cys Thr Ser Val Ile
        275                 280                 285

Leu Val Pro Thr Leu Phe Ala Ile Leu Asn Lys Ser Glu Leu Leu Asn
    290                 295                 300

Lys Tyr Asp Leu Ser Asn Leu Val Glu Ile Ala Ser Gly Gly Ala Pro
305                 310                 315                 320
```

```
        Leu  Ser  Lys  Glu  Val  Gly  Glu  Ala  Val  Ala  Arg  Arg  Phe  Asn  Leu  Pro
                       325                     330                          335

Gly  Val  Arg  Gln  Gly  Tyr  Gly  Leu  Thr  Glu  Thr  Thr  Ser  Ala  Ile  Ile
                       340                     345                     350

Ile  Thr  Pro  Glu  Gly  Asp  Asp  Lys  Pro  Gly  Ala  Ser  Gly  Lys  Val  Val
                       355                     360                          365

Pro  Leu  Phe  Lys  Ala  Lys  Val  Ile  Asp  Leu  Asp  Thr  Lys  Lys  Ser  Leu
                       370                     375                     380

Gly  Pro  Asn  Arg  Arg  Gly  Glu  Val  Cys  Val  Lys  Gly  Pro  Met  Leu  Met
        385                          390                     395                     400

Lys  Gly  Tyr  Val  Asn  Asn  Pro  Glu  Ala  Thr  Lys  Glu  Leu  Ile  Asp  Glu
                            405                     410                          415

Glu  Gly  Trp  Leu  His  Thr  Gly  Asp  Ile  Gly  Tyr  Tyr  Asp  Glu  Glu  Lys
                       420                     425                          430

His  Phe  Phe  Ile  Val  Asp  Arg  Leu  Lys  Ser  Leu  Ile  Lys  Tyr  Lys  Gly
                  435                     440                          445

Tyr  Gln  Val  Pro  Pro  Ala  Glu  Leu  Glu  Ser  Val  Leu  Leu  Gln  His  Pro
             450                          455                     460

Ser  Ile  Phe  Asp  Ala  Gly  Val  Ala  Gly  Val  Pro  Asp  Pro  Val  Ala  Gly
        465                     470                     475                          480

Glu  Leu  Pro  Gly  Ala  Val  Val  Val  Leu  Glu  Ser  Gly  Lys  Asn  Met  Thr
                            485                     490                          495

Glu  Lys  Glu  Val  Met  Asp  Tyr  Val  Ala  Ser  Gln  Val  Ser  Asn  Ala  Lys
                       500                     505                     510

Arg  Leu  Arg  Gly  Gly  Val  Arg  Phe  Val  Asp  Glu  Val  Pro  Lys  Gly  Leu
                       515                     520                     525

Thr  Gly  Lys  Ile  Asp  Gly  Arg  Ala  Ile  Arg  Glu  Ile  Leu  Lys  Lys  Pro
             530                          535                     540

Val  Ala  Lys  Met
        545
```

( 2 ) INFORMATION FOR SEQ ID NO:3:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: unknown     ( i i ) MOLECULE TYPE: Other nucleic acid     ( x i ) SEQUENCE DESCRIPTION: SEQ ID NO:3:

CGACAATGGA AAACATGGAA AACGATGAAA AT          32

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: unknown     ( i i ) MOLECULE TYPE: Other nucleic acid     ( x i ) SEQUENCE DESCRIPTION: SEQ ID NO:4:

ATTTTCATCG TTTTCCATGT TTTCCATTGT          30

( 2 ) INFORMATION FOR SEQ ID NO:5:

( i ) SEQUENCE CHARACTERISTICS:
        ( A ) LENGTH: 38 base pairs
        ( B ) TYPE: nucleic acid -continued ( C ) STRANDEDNESS: single
( D ) TOPOLOGY: unknown ( i i ) MOLECULE TYPE: Other nucleic acid ( x i ) SEQUENCE DESCRIPTION: SEQ ID NO:5:

CTCTAGCATG CGAAAATCTA GTGACTACAT TTTCGTGA           38

( 2 ) INFORMATION FOR SEQ ID NO:6:

( i ) SEQUENCE CHARACTERISTICS:
( A ) LENGTH: 38 base pairs
( B ) TYPE: nucleic acid
( C ) STRANDEDNESS: single
( D ) TOPOLOGY: unknown ( i i ) MOLECULE TYPE: Other nucleic acid ( x i ) SEQUENCE DESCRIPTION: SEQ ID NO:6:

CTCTAGCATG CGAAAATCTA GTGACGACAT TTTCGTGA           38

( 2 ) INFORMATION FOR SEQ ID NO:7:

( i ) SEQUENCE CHARACTERISTICS:
( A ) LENGTH: 1644 base pairs
( B ) TYPE: nucleic acid
( C ) STRANDEDNESS: single
( D ) TOPOLOGY: unknown ( i i ) MOLECULE TYPE: cDNA to mRNA ( x i ) SEQUENCE DESCRIPTION: SEQ ID NO:7:

| | | | | | |
|---|---|---|---|---|---|
| ATGGAAAACA | TGGAGAACGA | TGAAATATT | GTGTATGGTC | CTGAACCATT | TTACCCTATT | 60 |
| GAAGAGGGAT | CTGCTGGAGC | ACAATTGCGC | AAGTATATGG | ATCGATATGC | AAAACTTGGA | 120 |
| GCAATTGCTT | TTACTAACGC | ACTTACCGGT | GTCGATTATA | CGTACGCCGA | ATACTTAGAA | 180 |
| AAATCATGCT | GTCTAGGAGA | GGCTTTAAAG | AATTATGGTT | TGGTTGTTGA | TGGAAGAATT | 240 |
| GCGTTATGCA | GTGAAAACTG | TGAAGAATTC | TTTATTCCTG | TATTAGCCGG | TTTATTTATA | 300 |
| GGTGTCGGTG | TGGCTCCAAC | TAATGAGATT | TACACTCTAC | GTGAATTGGT | TCACAGTTTA | 360 |
| GGCATCTCTA | AGCCAACAAT | TGTATTTAGT | TCTAAAAAAG | GATTAGATAA | AGTTATAACT | 420 |
| GTACAAAAAA | CGGTAACTGC | TATTAAAACC | ATTGTTATAT | TGGACAGCAA | AGTGGATTAT | 480 |
| AGAGGTTATC | AATCCATGGA | CAACTTTATT | AAAAAAAACA | CTCCACAAGG | TTTCAAAGGA | 540 |
| TCAAGTTTTA | AAACTGTAGA | AGTTAACCGC | AAAGAACAAG | TTGCTCTTAT | AATGAACTCT | 600 |
| TCGGGTTCAA | CCGGTTTGCC | AAAAGGTGTG | CAACTTACTC | ATGAAAATGC | AGTCACTAGA | 660 |
| TTTTCTCACG | CTAGAGATCC | AATTTATGGA | AACCAAGTTT | CACCAGGCAC | GGCTATTTTA | 720 |
| ACTGTAGTAC | CATTCCATCA | TGGTTTTGGT | ATGTTTACTA | CTTTAGGCTA | TCTAACTTGT | 780 |
| GGTTTTCGTA | TTGTCATGTT | AACGAAATTT | GACGAAGAGA | CTTTTTTAAA | AACACTGCAA | 840 |
| GATTACAAAT | GTTCAAGCGT | TATTCTTGTA | CCGACTTTGT | TTGCAATTCT | TAATAGAAGT | 900 |
| GAATTACTCG | ATAAATATGA | TTTATCAAAT | TTAGTTGAAA | TTGCATCTGG | CGGAGCACCT | 960 |
| TTATCTAAAG | AAATTGGTGA | AGCTGTTGCT | AGACGTTTTA | ATTTACCGGG | TGTTCGTCAA | 1020 |
| GGCTATGGTT | TAACAGAAAC | AACCTCTGCA | ATTATTATCA | CACCGGAAGG | CGATGATAAA | 1080 |
| CCAGGTGCTT | CTGGCAAAGT | TGTGCCATTA | TTTAAAGCAA | AAGTTATCGA | TCTTGATACT | 1140 |
| AAAAAAACTT | TGGGCCCGAA | CAGACGTGGA | GAAGTTTGTG | TAAAGGGTCC | TATGCTTATG | 1200 |
| AAAGGTTATG | TAGATAATCC | AGAAGCAACA | AGAGAAATCA | TAGATGAAGA | AGGTTGGTTG | 1260 |
| CACACAGGAG | ATATTGGGTA | TTACGATGAA | GAAAAACATT | TCTTTATCGT | GGATCGTTTG | 1320 |
| AAGTCTTTAA | TCAAATACAA | AGGATATCAA | GTACCACCTG | CTGAATTAGA | ATCTGTTCTT | 1380 |

```
TTGCAACATC CAAATATTTT TGATGCCGGC GTTGCTGGCG TTCCAGATCC TATAGCTGGT    1440

GAGCTTCCGG GAGCTGTTGT TGTACTTGAA AAAGGAAAAT CTATGACTGA AAAAGAAGTA    1500

ATGGATTACG TTGCTAGTCA AGTTTCAAAT GCAAAACGTT TGCGTGGTGG TGTCCGTTTT    1560

GTGGACGAAG TACCTAAAGG TCTCACTGGT AAAATTGACG GTAAAGCAAT TAGAGAAATA    1620

CTGAAGAAAC CAGTTGCTAA GATG                                          1644
```

(2) INFORMATION FOR SEQ ID NO:8:

(i) SEQUENCE CHARACTERISTICS:
    (A) LENGTH: 548 amino acids
    (B) TYPE: amino acid
    (C) STRANDEDNESS: single
    (D) TOPOLOGY: unknown (ii) MOLECULE TYPE: peptide (xi) SEQUENCE DESCRIPTION: SEQ ID NO:8:

```
Met Glu Asn Met Glu Asn Asp Glu Asn Ile Val Tyr Gly Pro Glu Pro
 1               5                  10                  15

Phe Tyr Pro Ile Glu Glu Gly Ser Ala Gly Ala Gln Leu Arg Lys Tyr
                20                  25                  30

Met Asp Arg Tyr Ala Lys Leu Gly Ala Ile Ala Phe Thr Asn Ala Leu
            35                  40                  45

Thr Gly Val Asp Tyr Thr Tyr Ala Glu Tyr Leu Glu Lys Ser Cys Cys
        50                  55                  60

Leu Gly Glu Ala Leu Lys Asn Tyr Gly Leu Val Val Asp Gly Arg Ile
65                  70                  75                  80

Ala Leu Cys Ser Glu Asn Cys Glu Glu Phe Phe Ile Pro Val Leu Ala
                85                  90                  95

Gly Leu Phe Ile Gly Val Gly Val Ala Pro Thr Asn Glu Ile Tyr Thr
                100                 105                 110

Leu Arg Glu Leu Val His Ser Leu Gly Ile Ser Lys Pro Thr Ile Val
            115                 120                 125

Phe Ser Ser Lys Lys Gly Leu Asp Lys Val Ile Thr Val Gln Lys Thr
        130                 135                 140

Val Thr Ala Ile Lys Thr Ile Val Ile Leu Asp Ser Lys Val Asp Tyr
145                 150                 155                 160

Arg Gly Tyr Gln Ser Met Asp Asn Phe Ile Lys Lys Asn Thr Pro Gln
                165                 170                 175

Gly Phe Lys Gly Ser Ser Phe Lys Thr Val Glu Val Asn Arg Lys Glu
            180                 185                 190

Gln Val Ala Leu Ile Met Asn Ser Ser Gly Ser Thr Gly Leu Pro Lys
        195                 200                 205

Gly Val Gln Leu Thr His Glu Asn Ala Val Thr Arg Phe Ser His Ala
210                 215                 220

Arg Asp Pro Ile Tyr Gly Asn Gln Val Ser Pro Gly Thr Ala Ile Leu
225                 230                 235                 240

Thr Val Val Pro Phe His His Gly Phe Gly Met Phe Thr Thr Leu Gly
                245                 250                 255

Tyr Leu Thr Cys Gly Phe Arg Ile Val Met Leu Thr Lys Phe Asp Glu
            260                 265                 270

Glu Thr Phe Leu Lys Thr Leu Gln Asp Tyr Lys Cys Ser Ser Val Ile
        275                 280                 285

Leu Val Pro Thr Leu Phe Ala Ile Leu Asn Arg Ser Glu Leu Leu Asp
290                 295                 300

Lys Tyr Asp Leu Ser Asn Leu Val Glu Ile Ala Ser Gly Gly Ala Pro
```

|      |      |     |     |     |     |     |     |     |     |     |     |     |     |     |
|------|------|-----|-----|-----|-----|-----|-----|-----|-----|-----|-----|-----|-----|-----|
| 305  |      |     |     |     | 310 |     |     |     |     | 315 |     |     |     | 320 |
| Leu  | Ser  | Lys | Glu | Ile | Gly | Glu | Ala | Val | Ala | Arg | Arg | Phe | Asn | Leu | Pro |
|      |      |     |     | 325 |     |     |     |     | 330 |     |     |     | 335 |     |
| Gly  | Val  | Arg | Gln | Gly | Tyr | Gly | Leu | Thr | Glu | Thr | Thr | Ser | Ala | Ile | Ile |
|      |      |     | 340 |     |     |     |     | 345 |     |     |     | 350 |     |     |
| Ile  | Thr  | Pro | Glu | Gly | Asp | Asp | Lys | Pro | Gly | Ala | Ser | Gly | Lys | Val | Val |
|      |      | 355 |     |     |     |     | 360 |     |     |     |     | 365 |     |     |
| Pro  | Leu  | Phe | Lys | Ala | Lys | Val | Ile | Asp | Leu | Asp | Thr | Lys | Lys | Thr | Leu |
|      | 370  |     |     |     | 375 |     |     |     |     | 380 |     |     |     |     |
| Gly  | Pro  | Asn | Arg | Arg | Gly | Glu | Val | Cys | Val | Lys | Gly | Pro | Met | Leu | Met |
| 385  |      |     |     |     | 390 |     |     |     |     | 395 |     |     |     |     | 400 |
| Lys  | Gly  | Tyr | Val | Asp | Asn | Pro | Glu | Ala | Thr | Arg | Glu | Ile | Ile | Asp | Glu |
|      |      |     |     | 405 |     |     |     |     | 410 |     |     |     |     | 415 |     |
| Glu  | Gly  | Trp | Leu | His | Thr | Gly | Asp | Ile | Gly | Tyr | Tyr | Asp | Glu | Glu | Lys |
|      |      |     | 420 |     |     |     |     | 425 |     |     |     |     | 430 |     |     |
| His  | Phe  | Phe | Ile | Val | Asp | Arg | Leu | Lys | Ser | Leu | Ile | Lys | Tyr | Lys | Gly |
|      |      | 435 |     |     |     |     | 440 |     |     |     |     | 445 |     |     |     |
| Tyr  | Gln  | Val | Pro | Pro | Ala | Glu | Leu | Glu | Ser | Val | Leu | Leu | Gln | His | Pro |
|      | 450  |     |     |     |     | 455 |     |     |     |     | 460 |     |     |     |     |
| Asn  | Ile  | Phe | Asp | Ala | Gly | Val | Ala | Gly | Val | Pro | Asp | Pro | Ile | Ala | Gly |
| 465  |      |     |     |     | 470 |     |     |     |     | 475 |     |     |     |     | 480 |
| Glu  | Leu  | Pro | Gly | Ala | Val | Val | Val | Leu | Glu | Lys | Gly | Lys | Ser | Met | Thr |
|      |      |     |     | 485 |     |     |     |     | 490 |     |     |     |     | 495 |     |
| Glu  | Lys  | Glu | Val | Met | Asp | Tyr | Val | Ala | Ser | Gln | Val | Ser | Asn | Ala | Lys |
|      |      |     | 500 |     |     |     |     | 505 |     |     |     |     | 510 |     |     |
| Arg  | Leu  | Arg | Gly | Gly | Val | Arg | Phe | Val | Asp | Glu | Val | Pro | Lys | Gly | Leu |
|      |      | 515 |     |     |     |     | 520 |     |     |     |     | 525 |     |     |     |
| Thr  | Gly  | Lys | Ile | Asp | Gly | Lys | Ala | Ile | Arg | Glu | Ile | Leu | Lys | Lys | Pro |
|      |      | 530 |     |     |     |     | 535 |     |     |     |     | 540 |     |     |     |
| Val  | Ala  | Lys | Met |     |     |     |     |     |     |     |     |     |     |     |     |
| 545  |      |     |     |     |     |     |     |     |     |     |     |     |     |     |     |

( 2 ) INFORMATION FOR SEQ ID NO:9:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: unknown     ( i i ) MOLECULE TYPE: Other nucleic acid     ( x i ) SEQUENCE DESCRIPTION: SEQ ID NO:9:

AGCGTGAGAA AAACGCGTGA CGACATTTTC ACGAGT      36

( 2 ) INFORMATION FOR SEQ ID NO:10:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: unknown     ( i i ) MOLECULE TYPE: Other nucleic acid     ( x i ) SEQUENCE DESCRIPTION: SEQ ID NO:10:

AGCGTGAGAA AAACGCGTGA CCAAATTTTC ACGAGT      36

( 2 ) INFORMATION FOR SEQ ID NO:11:

( i ) SEQUENCE CHARACTERISTICS:
        ( A ) LENGTH: 36 base pairs ( B ) TYPE: nucleic acid
( C ) STRANDEDNESS: single
( D ) TOPOLOGY: unknown ( i i ) MOLECULE TYPE: Other nucleic acid ( x i ) SEQUENCE DESCRIPTION: SEQ ID NO:11:

AGCGTGAGAA AAACGCGTGA CGATATTTTC ACGAGT  36

THERMOSTABLE LUCIFERASE OF FIREFLY, THERMOSTABLE LUCIFERASE GENE OF FIREFLY, NOVEL RECOMBINANT DNA, AND PROCESS FOR THE PREPARATION OF THERMOSTABLE LUCIFERASE OF FIREFLY

FIELD OF THE INVENTION

The present invention relates to thermostable luciferase of firefly, a gene of thermostable luciferase of firefly, novel recombinant DNA, and a process for the preparation of thermostable luciferase of firefly.

BACKGROUND OF THE INVENTION

Luciferase is a luminescence enzyme which catalyzes oxidation of luciferin, thus allowing it to emit a light. Luciferase derived from fireflies, such as GENJI firefly, HEIKE firefly, American firefly, etc., requires ATP, etc., for the luminescence of luciferin, and owing to this property, luciferase is used for the quantitative determination of a trace amount of the above-mentioned ATP, etc.

However, since luciferase is generally unstable to heat, this enzyme has the defect of being liable to be inactivated in storage as a reagent. As a means of avoiding this disadvantage, the addition of a salt, etc., makes it possible to store luciferase stable to some extent. In this case, however, the presence of the salt sometimes leads to another disadvantage, i.e. hindrance of luciferase reaction.

SUMMARY OF THE INVENTION

As a result of extensive researches, the present inventors have found that the above object can be solved by converting a amino acid residue at a specific position into a hydrophobic amino acid residue. sequence of wild-type firefly luciferase in which an amino acid at the 217-position or an amino acid at the position equivalent to the 217-position of luciferase of *Luciola cruciata* (GENJI firefly) or *Luciola lateralis* (HEIKE firefly) is replaced by a hydrophobic amino acid.

2. Gene of thermostable luciferase of firefly according to claim 1, wherein the wild-type firefly luciferase is luciferase of *Luciola lateralis* (HEIKE firefly) or *Luciola cruciata* (GENJI firefly).

3. Gene of thermostable luciferase of firefly according to claim 1 or 2, wherein the hydrophobic amino acid is isoleucine, leucine, or valine.

4. Recombinant DNA, which comprises the gene of thermostable luciferase of firefly according to claim 1 or 2 inserted into vector DNA.

5. Process for the preparation of thermostable luciferase of firefly, which comprises incubation in a culture medium of a microorganism belonging to the genus Escherichia, carrying the recombinant DNA according to claim 4 and being capable of producing thermostable luciferase of firefly, and subsequent collection of thermostable luciferase of firefly from said culture medium.

6. Thermostable luciferase of firefly, wherein an amino acid at the 217-position of the amino acid sequence of wild-type firefly luciferase or an amino acid at the position equivalent to the 217-position of luciferase of *Luciola cruciata* (GENJI firefly) or *Luciola lateralis* (HEIKE firefly) is replaced by a hydrophobic amino acid.

7. Thermostable luciferase of firefly according to claim 6, wherein the wild-type firefly luciferase is luciferase of *Luciola lateralis* (HEIKE firefly) or *Luciola cruciata* (GENJI firefly).

DETAILED DESCRIPTION OF THE INVENTION

The main object of the invention is to develop thermostable luciferase of firefly.

The invention is described in detail hereinafter.

As a precondition for providing thermostable luciferase by the present method of gene mutation, it is necessary to prepare the gene of a wild-type firefly and its recombinant DNA.

The types of wild-type firefly gene, etc., are adopted depending on the type of thermostable luciferase gene attempted. Any types of genes can be used if they are derived from fireflies such as e.g. *Luciola cruciata* (GENJI firefly), *Luciola lateralis* (HEIKE firefly), etc. These genes, etc., are prepared according to the method known in the art. For example, a wild-type firefly gene and its recombinant DNA can be prepared according to the method as disclosed in Japanese Patent Appln. LOP Publication No. 51,086/1989.

In the present invention, "an amino acid at the position equivalent to the 217-position of luciferase of GENJI firefly or HEIKE firefly" means an amino acid which corresponds to the amino acid at the 217-position of the amino acid sequence of luciferase of GENJI firefly or HEIKE firefly, as a result of the comparison of the established luciferase amino acid sequence with the amino acid sequence of luciferase of GENJI firefly or HEIKE firefly.

Specifically, this is determined by comparison of the homology between the amino acid sequence of each luciferase and the amino acid sequence of GENJI or HEIKE firefly using commercially available software for analysis of homology, e.g. Micro Genie ™ (manufactured by Beckman). Although the corresponding amino acids are not particularly limited, they are e.g. threonine or alanine.

In the present invention, "a hydrophobic amino acid" includes isoleucine, leucine, valine, methionine, tryptophan, phenylalanine, proline, cysteine, and alanine. Among these amino acids, isoleucine, leucine, or valine are particularly preferred due to their high hydrophobicity. Mutagenesis of the gene of wild-type firefly luciferase can be effected according to the method known in the art, depending on attempted mutagenesis.

That is, it is possible to adopt a broad scope of methods: e.g. a method comprising allowing a chemical as mutagen to contact and act on the wild-type firefly luciferase gene or the recombinant DNA having said gene inserted; a ultraviolet irradiation method; a means of genetic engineering; and a means of protein engineering.

Chemicals acting as mutagen for use in said mutagenesis include e.g. hydroxylamine, N-methyl-N'-nitro-N-nitrosoguanidine (NTG), nitrous acid, sulfurous acid, hydrazine, formic acid, 5-bromouracil, etc.

Conditions for the application can vary depending on the type, etc., of chemicals used, and these conditions are not particularly limited, insofar as the mutagenesis of the wild-type firefly luciferase gene is virtually brought about as desired.

Mutagenesis by ultraviolet irradiation can also be effected according to the conventional method as described above (Gendai Kagaku (Japan), 24–30, the June issue of 1989).

As a method of making full use of protein engineering, a means generally known as site-specific mutagenesis can be employed: e.g. the Kramer method (Kramer, W. et al., Nucleic Acids Res, 12: 9,441–9,456 (1984): Kramer, W. et al., Methods Enzymol, 154: 350–367 (1987): Bauer, C. E. et al., Gene, 37: 73–81 (1985)), the Eckstein method (Taylor, J. W. et al., Nucleic Acids Res, 13: 8,749–8,764 (1985): Taylor, J. W. et al., Nucleic Acids Res, 13: 8,765–8,785 (1985): Nakamaye, K. L. et al., Nucleic Acids Res, 14: 9,679–9,698 (1986)), the Kunkel method (Kunkel. T. A., Proc. Natl. Acid. Sci. U.S.A., 88: 488–492 (1985): Kunkel. T. A. et al., Methods Enzymol, 154: 367–382 (1987)), etc.

In addition to the above-mentioned gene mutagenesis method, it is of course possible to directly synthesize a desired modified luciferase gene of firefly through organic or enzymatic synthesis.

The determination and identification of the base sequence of a desired luciferase gene of firefly can be effected e.g. through the chemical modification method as described by Maxam-Gilbert (Maxam-Gilbert, Meth. Enzym., 65: 499–560 (1980)), the dioxynucleotide termination procedure using M13 phage (Messing et al., Gene, 19: 269–276 (1982)), etc.

The gene of thermostable luciferase prepared as described above can be inserted into vectors, such bacteriophages, cosmids, or plasmids used for transformation of procaryotic or eucaryotic cells, according to the conventional method. Subsequently, the resulting vectors can be used for transformation or transduction of hosts at which said vector to be directed, in accordance with the known method in the art.

In case bacteria belonging to the genus Escherichia, e.g. E. coli JM101 (ATCC 33876), E. coli DH1 (ATCC 33849), E. coli HB101 (ATCC 33694), etc., are selected as hosts, they can be transformed by the method as described by Hana-han (DNA Cloning, 1: 109–135 (1985) or transduced by the method (Molecular Cloning, 256–268, Cold Spring Harbor Laboratory (1982)), whereby their transformed or transduced strain can be obtained.

A bacterial strain belonging to the genus Escherichia, carrying recombinant DNA having the gene of thermostable firefly luciferase inserted into vector DNA and being capable of producing thermostable firefly luciferase can be obtained from the above bacterial strain by screening the bacterial strain with the ability to produce thermostable firefly luciferase.

Novel recombinant DNA purified from the thus obtained bacterial strain can be prepared according to the method described e.g. by P. Guerry et al. (J. Bacteriology, 116: 1,064–1,066 (1973)), D. B. Clewell (J. Bacteriology, 110: 667–676 (1972)).

In order to prepare DNA containing the gene of thermostable firefly luciferase, the recombinant plasmid DNA thus obtained is digested e.g. with restriction enzymes such as Eco RI and Pst I at 30° to 40° C., preferably about 37° C., and for 1 to 24 hours, preferably about 2 hours, followed by subjection to agarose gel electrophoresis in accordance with the method (Molecular Cloning, p. 150, Cold Spring Harbor Laboratory (1982)), whereby the DNA containing said luciferase gene can be obtained.

For production of thermostable firefly luciferase, it is possible to use a usual solid medium, but it is preferable to use a liquid medium as far as circumstances permit, in order to culture the bacteria strain belonging to the genus Escherichia, carrying the recombinant DNA having the gene of thermostable firefly luciferase inserted into vector DNA and being capable of producing thermostable luciferase of firefly.

The bacterial strain is cultured in a medium in which e.g. one or more inorganic salts among sodium chloride, potassium dihydrogen phosphate, dipotassium hydrogen phosphate, magnesium sulfate, magnesium chloride, ferric chloride, ferric sulfate, manganese sulfate, etc., are added to one or more nitrogen sources among yeast extract, trypton, peptone, meat extract, corn steep liquor and exudate of soybean or wheat bran, and if necessary, sugars (or carbohydrates), vitamins, etc., are suitable added.

The initial pH value of the culture medium is suitable adjusted to 7–9.

Cultivation is carried out at 30° to 42° C., preferably about 37° C., and for 4 to 24 hours, preferably 6 to 8 hours, and preferably effected by submerged aeration culture, shake culture, or stationary culture.

After cultivation, mutant luciferase is recovered from the culture according to the methods known in the art:

For example, the present enzyme can be extracted from bacteria bodies by disrupting the cells using ultrasonication and crushing; by treatment with a lytic enzyme such as lysozyme; or by autolysis of bacteria bodies in the presence of toluene, etc., with or without shaking. The lysate is filtered or centrifuged for removal of cells and cell debris. If it is necessary to remove nucleic acids, streptomycin sulfate, protamine sulfate, or manganese sulfate is added to the filtrate or the supernatant. The mixture is then fractionated by addition of ammonium sulfate, alcohols, acetone, etc., thereby giving precipitates as crude enzyme.

For the preparation of a purified enzyme standard, crude enzyme thus obtained may be purified by a method or the suitable combination of methods which include gel filtration by Sephadex, Ultro-Gel, or Bio-Gel; an adsorption-elution method by ion exchanger; electrophoresis by polyacrylamide gel, etc.; an adsorption-elution method by hydroxyapatite; precipitation by sucrose density-gradient centrifugation, etc.; affinity chromatography; and fractionation by molecular sieve membrane, hollow fiber membrane, etc.

According to the method as illustrated above, desired thermostable luciferase of firefly can be obtained. The present thermostable luciferase of firefly is characterized by the following properties:

(1) Suitable working temperature range:

The suitable temperature for the action ranges from 0° to 65° C.

(2) Inactivation conditions of pH, temperature, etc.:

i) The enzyme is completely inactivated at pH values of 4.0 or lower or 12.0 or more, 4 hours after.

ii) The enzyme is completely inactivated by heating at a temperature of 65° C. at pH 7.8, 60 minutes after.

(3) Thermostability:

80% or more of enzyme activity remains at a temperature of 50° C. 20 minutes after, and 65% or more of enzyme activity remains by heating at a temperature of 50° C., even 60 minutes after.

Except for the above properties, the present enzyme is identical with luciferase of wild-type GENJI firefly as disclosed in Japanese Patent Appln. LOP Publication No. 141,189 and of wild-type HEIKE firefly as disclosed in Japanese Patent Appln. LOP Publication No. 262,791/1989.

EXAMPLES

The following Examples further illustrate the invention.

Sections (1) to (10) below describe the construction of DNA containing the gene encoding luciferase of a firefly, *Photinus pyralis*. (Said DNA is used as a probe for screening DNA containing the gene encoding luciferase of the firefly *Luciola cruciata*).

(1) Preparation of m-RNA 1 g of dried tails of the firefly *Photinus pyralis* (manufactured by Sigma Co., Ltd.) was sufficiently disrupted and ground in a mortar using a pestle, followed by addition of 5 ml of a dissolution buffer [20 mM Tris-HCl buffer (pH 74), 10 mM NaCl, 3 mM magnesium acetate, 5% (W/V) sucrose, 1.2% (V/V) Triton X-100, and 10 mM vanadyl nucleoside complex (produced by New England Biolabs]. The sample was further disrupted and ground in the same way as above, whereby a solution containing the disrupted tails of *Photinus pyralis* was obtained.

5 ml of the solution thus obtained was introduced into a cup type blender (manufactured by Nippon Seiki Seisakusho Co.) and blended at 5,000 r.p.m. for 5 min. 12 ml of a guanidine isocyanate solution (6 M guanidine isocyanate, 37.5 mM sodium citrate (pH 7.0), 0.75% (W/V) sodium N-lauroylsarcosinate, and 0.15 M β-mercaptoethanol) was added to the sample solution. This solution was further blended at 3,000 r.p.m. for 10 min. using the above blender. The mixture was then filtered through a three-folded gauze, whereby a filtrate was obtained. Subsequently, the filtrate was pipetted and layered onto 4 ultracentrifugation tubes (manufactured by Hitachi Koki Co.) so as to be stacked on 1.2 ml of 5.7 M cesium chloride previously placed in each tube. The sample was centrifuged at 30,000 r.p.m. for 16 hours at a temperature of 15° C. (SCP55H ultracentrifuge manufactured by Hitachi Koki Co.), so that precipitates were obtained. The precipitates thus obtained were washed with cold 70% (V/V) ethanol and were then suspended in 4 ml of 10 mM Tris-HCl buffer [10 mM Tris-HCl buffer (pH 7.4), 5 mM EDTA, and 1% sodium dodecyl sulfate]. The mixture was extracted with an equal volume of n-butanol and chloroform (4:1 [V/V]). The extract was centrifuged over 10 min. at 3,000 r.p.m. in accordance with a conventional manner, whereby the solution was separated into an aqueous layer and organic solvent layer, and the former was saved, 4 ml of 10 mM Tris-HCl buffer of the same composition as above was added to the organic solvent phase. The organic phase was back-extracted twice in the same manner as described above, and the aqueous phase was pooled each time. To the combined aqueous phase, 1/10 volume of 3 M sodium acetate (pH 5.2) and two volumes of cold ethanol were added. The mixture was allowed to stand for 2 hours at a temperature of −20° C. and was then centrifuged at 8,000 r.p.m. for 20 min. in accordance with the conventional manner, whereby RNA was precipitated. The RNA thus obtained was dissolved in 4 ml water and was then precipitated with ethanol in the same manner as above.

The RNA obtained was resuspended in 1 ml water, and 3.75 mg RNA were obtained.

7 mg of RNA in total were prepared by repeating the above procedure. In order to separate m-RNA from RNA, 7 mg of the RNA were applied to oligo(dT)-cellulose (produced by New England Biolabs) column chromatography.

For column chromatography, the column was prepared as follows: 0.5 g of the resin was swelled with an eluting buffer [10 mM Tris-HCl buffer (pH 7.6), 1 mM EDTA, and 0.1% (W/V) sodium dodecyl sulfate] and was then packed into a 2.5 ml Terumo syringe (manufactured by Terumo) used as a column, and the column was equilibrated with a binding buffer [10 mM Tris-HCl (pH 7.6), 1 mM EDTA, 0.4 M NaCl, and 0.1% sodium dodecyl sulfate].

An equal volume of a buffer [10 mM Tris-HCl (pH 7.6), 1 mM EDTA, and 0.8 M NaCl, and 0.1% sodium dodecyl sulfate] was added to the RNA (7 mg) suspension. This mixture was heated at 65° C. for 10 min. and then rapidly cooled on ice. The sample thus treated was applied to an oligo(dT)-cellulose column as prepared above, and the resin was washed with the binding buffer, whereby unbound r-RNA and t-RNA were completely washed out. Then, m-RNA was eluted with the eluting buffer, so that 40 μg of m-RNA were obtained.

(2) Concentration of Luciferase m-RNA

Subsequently, luciferase m-RNA was concentrated by sucrose density-gradient centrifugation.

A 10 to 25% (W/V) sucrose density-gradient was prepared as follows: 0.5 ml of a 40% (W/V) sucrose solution [50 mM Tris-HCl buffer (pH 7.5), 20 mM NaCl, 1 mM EDTA, and 40% (W/V) sucrose] was introduced into a polyaroma tube for Rotor SW41 manufactured by Beckman, and on said sucrose solution was layered 2.4 ml of each sucrose (25% (W/V), 20% (W/V), 15% (W/V), and 10% (W/V)), and they were allowed to stand over 24 hours. Then, 30 μg of m-RNA were layered on the sucrose gradient, which in turn was centrifuged at 30,000 r.p.m. over 18 hours at a temperature of 18° C. in accordance with the conventional manner. After centrifugation, the sample was fractionated into 0.5 ml per fraction, and the m-RNA was recovered by ethanol precipitation and was resuspended in 10 μl water.

Then, a protein encoded by m-RNA was examined for identification of the fraction containing a high level of luciferase m-RNA. 1 μl of the fractionated RNA, 9 μl of rabbit reticulocyte lysate (produced by Amersham), and 1 μl of [$^{35}$S] methionine (produced by Amersham) were mixed, and the mixture was allowed to react at 30° C. for 30 min. After 150 μl NET buffer [150 mM NaCl, 5 mM EDTA, 0.02% (W/V) NaN$_3$, 20 mM Tris-HCl buffer (pH 7.4), and 0.05% (W/V) Nonidet P-40 (BR detergent)] and 1 μl of anti-luciferase serum (which was prepared according to the method as described below) were added to said mixture, it was allowed to stand at 4° C. for 18 hours. Subsequently, 10 mg of protein A Sepharose (produced by Pharmacia AG) were added thereto, and the sample solution was allowed to stand at a temperature of 20° C. for 30 min., followed by centrifugation for 1 min. at 12,000 r.p.m. in accordance with a conventional manner, whereby the resin was recovered.

The recovered resin was washed 3 times with 200 μl NET buffer, and then 40 μl of a sample buffer for SDS- PAGE [62.5 mM Tris-HCl buffer (pH 6.8), 10% (V/V) glycerol, 2% (W/V) sodium dodecyl sulfate, 5% (V/V) mercaptoethanol, and 0.02% (W/V) Bromophenol Blue] was added to said resin, which was then boiled for 3 min. at 100° C. and centrifuged at 12,000 r.p.m. for 1 min. in accordance with the conventional manner. The supernatant obtained in this centrifugation was recovered, and the whole amount of the supernatant was subjected to gel electrophoresis on a 7.5% (W/V) sodium dodecyl sulfate-polyacrylamide gel according to the method as described by Laemmli [Nature, p. 227, p. 680 (1970)].

Following gel electrophoresis, the gel was immersed in 10% (V/V) acetic acid for 30 min. whereby proteins were immobilized, followed by immersion in water for 30 min. and then in 1M sodium salicylate for 30 min., and the gel was dried. Fluorography of the dried gel was conducted by exposure to X-ray film RX (manufactured by Fuji Film Co.).

According to the above procedure, the presence of a band on the film indicated the presence of an elevated level of luciferase m-RNA in that fraction, so that the concentrated luciferase m-RANA fraction could be identified.

(3) Preparation of Anti-luciferase Serum

Rabbit anti-luciferase serum against purified luciferase was prepared according to the following method.

0.7 ml of luciferase solution (3.2 mg/ml) [luciferase (Sigma) was dissolved in 0.5M glycylglycine solution (pH 7.8)] is mixed with an equal volume of Freund's complete adjuvant]. The mixture was administered as an antigen into a Japanese white rabbit at the pad with a body weight of 2 kg.

Two weeks thereafter, the same amount of the antigen-adjuvant mixture was intracutaneously administered into the rabbit at the back. One week thereafter, the same procedure was carried out and then sacrificed and bled. The blood thus obtained was left standing stand over 18 hours at a temperature of 4° C. and then centrifuged over 15 min. at 3,000 r.p.m. according to the conventional manner, so that an anti-luciferase serum was obtained as a supernatant.

(4) Synthesis of c-DNA

Synthesis of c-DNA was carried out using a kit produced by Amersham.

2 μg of the m-RNA obtained above were treated according to the method described in Mol. Cell Biol., 2, 161 (1982) and Gene, 25, 263 (1983) as recommended by the manufacturer's instructions, whereby 300 ng of double-stranded c-DNA were obtained.

150 ng of the c-DNA were dissolved in 7 μl of a TE buffer [10 mM Tris-HCl buffer (pH 7.5) and 1 mM EDTA]. 11 μl of a mixture solution [280 mM sodium cacodylate (pH 6.8), 60 mM Tris-HCl (pH 6.8), and 2 mM cobalt chloride], 3.8 μl of a tailing mixture solution [7.5 μl of 10 mM dithiothreitol, 1 μl of 10 ng/ml polyA, 2 μl of 5 mM dCTP, and 100 μl water], and 29 units of terminal transferase (produced by Boehringer Mannheim GmbH) were added to the sample solution. This solution was allowed to react at 30° C. for 10 min., and then 2.5 μl of 0.25M EDTA and 2.4 μl of 10% (W/V) sodium dodecyl sulfate were added to the mixture to stop the reaction.

Subsequently, this sample solution was treated with 25 μl of water-saturated phenol for removal of proteins. The aqueous layer was recovered, and 25 μl of 4M ammonium acetate and 100 μl of cold ethanol were added to the aqueous portion. The mixture was allowed to stand at −70° C. for 15 min. and was then centrifuged at 12,000 r.p.m. for 10 min., whereby the c-DNA was recovered. The c-DNA was dissolved in 10 μl TE buffer to give a solution of c-DNA. According to the above procedure, 100 ng of deoxycytidine-tailed c-DNA were obtained.

(5) Preparation of Recombinant Plasmid DNA pMCE10 Used as Vector

According to the method as described by T. Masuda et al. (AgricuLtd. ural Biological Chemistry, 50: 271–279 (1986)), plasmid DNA pKN305 and plasmid DNA pMC457 1403-3 (disclosed in Japanese Patent Appln. LOP Publication No. 274,683/1986) were respectively constructed using E. coli strain W3110 (ATCC 27325), plasmid DNA pBR325 (produced by BRL), and plasmid DNA pBR322 (produced by Takara Shuzo Co., Ltd.). 1 μg of each plasmid was added to 10 μl of a mixture solution [50 mM Tris-HCl buffer (pH 7.5), 10 mM $MgCl_2$, 100 mM NaCl, and 1 mM dithiothreitol] in a separate tube. Following addition of 2 units each of Hind III and Sal I (which are produced by Takara Shuzo Co., Ltd.), the sample was cleaved at 37° C. for 1 hour and was then extracted with phenol and precipitted with ethanol in accordance with the conventional manner, so that precipitates were obtained. The precipitates were dissolved in 10 μl of a ligation buffer [20 mM $MgCl_2$, 66 mM Tris-HCl buffer (pH 7.6), 1 mM ATP, and 15 mM dithiothreitol]. After 1 unit of T4 DNA ligase (produced by Takara Shuzo Co., Ltd.) was added, the sample was ligated at 20° C. for 4 hours. Subsequently, the sample solution thus reacted was transformed into E. coli strain JM101 (ATCC 33876) in accordance with the transformation method (J. Bacteriology, 119: 1,072–1074 (1974)). Then the E. coli was examined for drug tolerance (ampicillin resistance and tetracycline sensitivity) as well as for β-galactosidase activity, so that a transformant strain was obtained. Recombinant plasmid DNA contained in the transformant strain was named pMCE10. The E. coli strain JM101 carrying the recombinant plasmid DNA pMCE10 was incubated at 37° C. for 16 to 24 hours in a medium consisting of 1% (W/V) trypton, 0.5% (W/V) yeast extract, and 0.5% (W/V) NaCl. Then, 20 ml culture liquid of the E. coli strain JM 101 (pMCE10) was inoculated into 1 l of a medium of the same composition as described above and was incubated at 37° C. for 3 hours under shaking. Subsequently, 0.2 g chloramphenicol was added and the incubation was continued for further 20 hours at the same temperature, so that a culture liquid was obtained.

Then, the culture liquid was centrifuged at 6,000 r.p.m. for 10 min., to give 2 g wet bacteria bodies. The bacteria were suspended in 20 ml of 350 mM Tris-HCl buffer (pH 8.0) containing 25% (W/V) sucrose, followed by addition of 10 mg lysozyme, 8 ml of 0.25M EDTA solution (pH 8.0), and 8 ml of 20% (W/V) sodium dodecyl sulfate solution, and the mixture was kept at 60° C. for 30 min., whereby a solution of lysed bacteria was obtained.

13 ml of 5M NaCl was added to the solution of lysed bacteria, and this mixture was kept at 4° C. for 16 hours and then centrifuged at 15,000 r.p.m. for 30 min. according to the conventional manner, whereby an extract solution was obtained. This extract was subjected to phenol extraction and ethanol precipitation in accordance with the conventional manner, thereby giving precipitates.

Subsequently, the precipitates were dried under reduced pressure as usually carried out, and were then dissolved in 6 ml of 10 mM Tris-HCl buffer (pH 7.5) containing 1 mM EDTA, followed by addition of 6 g cesium chloride and 0.2 ml (10 mg/ml) ethidium bromide solution. Then, the sample mixture was subjected to equilibrium density-gradient centrifugation at 39,000 r.p.m. for 42 hours using a ultracentrifuge in accordance with the conventional manner, whereby a sample composed of the recombinant plasmid DNA pMCE10 was isolated. Then, the sample was extracted with n-butanol to remove ethidium bromide. The DNA solution was dialyzed against 10 mM Tris-HCl buffer (pH 7.5) containing 1 mM EDTA, so that 500 µg of purified recombinant plasmid DNA pMCE10 were obtained.

(6) Preparation of Vector DNA

15 µg of the recombinant plasmid DNA pMCE10 thus prepared were dissolved in 90 µl of TE buffer whose composition is described in (4) above, followed by addition of 10 µl of a Med buffer [100 mM Tris-HCl buffer (pH 7.5), 100 mM $MgCl_2$, 10 mM dithiothreitol, and 500 mM NaCl]. After 30 units of restriction enzyme Acc I (produced by Takara Shuzo Co., Ltd.) were further added, the sample was digested at 37° C. for 1 hour, whereby a cleaved sample was obtained. 100 µl of water-saturated phenol was added thereto for removal of proteins, and then an aqueous layer was recovered. To this aqueous layer were added 1/10 volume of 3M sodium acetate (pH 7.5) and two volumes of cold ethanol, and the mixture was kept at −70° C. for 15 min. and then centrifuged at 12,000 r.p.m. for 10 min., whereby DNA was recovered.

The DNA was dissolved in 10 µl of TE buffer, followed by addition of 15 µl of a mixture [280 mM sodium cacodylate (pH 6.8), 60 mM Tris-HCl buffer (pH 6.8), and 2 mM cobalt chloride], 5 µl of a (5 mM dGTP-containing) tailing mixture (described in (4) above), and 5 units of terminal transferase (produced by Takara Shuzo Co., Ltd.), and the sample mixture was allowed to react at 37° C. for 15 min. The rest of the procedure was carried out as in the c-DNA tailing reaction described in (4) above, whereby the recombinant plasmid DNA pMCE10 with a deoxyguanosine tail at the Acc I site was prepared.

Separately, the recombinant plasmid DNA pUC19 with a deoxyguanosine tail at the Pst I site was also prepared as follows.

30 µg of plasmid DNA pUC19 (produced by Takara Shuzo Co., Ltd.) was dissolved in 350 µl TE buffer. Following addition of 40 µl of Med buffer and 120 units of restriction enzyme Pst I (produced by Takara Shuzo Co., Ltd.), the sample was incubated at 37° C. for 1 hour. After digestion, the mixture was extracted with phenol. Then, DNA was precipitated with ethanol, whereby DNA was recovered.

The DNA thus obtained was dissolved in 35 µl of TE buffer, followed by addition of 50 µl of a mixture [280 mM sodium cacodylate (pH 6.8), 60 mM Tris-HCl buffer (pH 6.8), and 1 mM cobalt chloride], 19 µl of a (dGTP-containing) tailing mixture described in (4) above, and 60 units of terminal transferase (produced by Takara Shuzo Co., Ltd.). The sample mixture was allowed to react at 37° C. for 10 min. According to the conventional manner, the sample mixture was treated with phenol and DNA was recovered by ethanol precipitation.

(7) Annealing and Transformation 15 ng of synthesized c-DNA and 200 ng each of the two types of vector DNA prepared in the above method were dissolved in 35 µl of an annealing solution [10 mM Tris-HCl buffer (pH 7.5), 100 mM NaCl, and 1 mM EDTA] in a separate tube, and the mixture was allowed to stand at 65° C. for 2 min., at 46° C. for 2 hours, at 37° C. for 1 hour, and then at 20° C. for 18 hours, whereby the c-DNA and the vector DNA were annealed. The constructs were transformed into *E. coli* strain DH1 (ATCC 33849) according to the method as described by Hana-han (DNA Cloning, 1: 109–135 (1985)), and c-DNA libraries were prepared in which the plasmid DNA pUC19 and the recombinant plasmid DNA pMCE10, respectively, are vectors.

(8) Screening of Luciferase c-DNA

The Acc I site of the recombinant plasmid DNA pMCE10 was located in the region coding for an *E. coli* β-galactosidase gene, so that the c-DNA having been inserted into this region produced a fusion protein bound to β-galactosidase. The promoter of the β-galactosidase gene of recombinant plasmid DNA pMCE10 had been replaced by that of the tryptophan gene of *E. coli* as described previously.

96 colonies from the c-DNA library in which the recombinant plasmid DNA pMCE10 is a vector were incubated at 37° C. for 10 hours under shaking in an M9 casamino acid medium (Molecular Cloning, pp. 440–441, Cold Spring Harbor Laboratory (1982)) containing (10 µg/ml) thiamine. Then, the bacteria cells were collected according to the conventional manner and then suspended in 200 µl of sample buffer for SDS-PAGE as described in (2) above, and the suspension was boiled over 5 min. at 100° C.

40 µl of the suspension was electrophoresed in a 7.5% (W/V) polyacrylamide gel in accordance with the conventional method. After electrophoresis, the proteins developed in the gel were transferred to a nitrocellulose filter according to the Western blot analysis (Anal. Biochem., 112: 195 (1981)). This nitrocellulose filter was treated with anti-luciferase serum using an immunoblot assay kit (produced by Bio-Rad) according to the method recommended by manufacturer's instructions. That is, a nitrocellulose filter was shaken at 25° C. for 30 min. in 100 ml of 3% (W/V) blocking solution [in which 3% (W/V) gelatin is dissolved in a TBS buffer (20 mM Tris-HCl buffer (pH 7.5), 500 mM NaCl]. Then, the nitrocellulose filter was transferred to 25 ml of a primary antibody solution [in which luciferase antiserum is diluted 1:25 (V/V) with a TBS buffer containing 1% (W/V) gelatin] and shaken at 25° C. for 90 min. This filter was then transferred to 100 ml of Tween-20 Wash [in which 0.05% (W/V) Tween-20 is dissolved in TBS buffer] and shaken at 25° C. for 10 min., and this washing procedure was repeated one more time. Subsequently, the nitrocellulose filter thus treated was transferred to 60 ml of a secondary antibody solution [in which a horseradish peroxidase-labelled anti-rabbit antibody (produced by Bio-Rad) is diluted 1:3000 (V/V) with TBS buffer containing 1% (W/V) gelatin], followed by shaking at 25° C. for 60 min. Then, the nitrocellulose filter was washed twice with 100 ml of Tween-20 Wash, and this washing was repeated. The nitrocellulose filter thus treated was transferred to 120 ml of a staining solution [i.e. a mixture in which 20 ml of cold methanol having 60 mg of 4-chloro-1-naphthol dissolved is mixed with 100 ml TBS buffer containing 60 μl of 30% (V/V) hydrogen peroxide], followed by staining at 25° C. for 10 min.

Manipulating 96 colonies as a set, we screened additional three sets of colonies as described above. Two sets were positive. The two sets were further tested: The two sets of colonies were divided into 16 groups (12 colonies per group). The 16 groups were screened as described above. Of these, two groups were positive. 24 colonies were then screened individually as described above. Of these, two positive colonies were found and plasmid DNA of the two colonies was prepared as described in (5) above.

The plasmid DNAs were named pALf2B8 and pALf-3A6, respectively.

(9) Screening of Large Luciferase c-DNA (Preparation of DNA Probe)

100 μg of the recombinant plasmid DNA pALf3A6 were dissolved in 330 μl TE buffer, followed by addition of 40 μl of Low buffer [100 mM Tris-HCl buffer (pH 7.5), 100 mM $MgCl_2$, and 10 mM dithiothreitol], 130 units of Pst I (produced by takara Shuzo Co., Ltd.), and 120 units of Sac I (produced by Boehringer Mannheim GmbH), and the sample was cleaved at 37° C. for 1.5 hours. The total amount of DNA was separated by electrophoresis in a 0.7% (W/V) agarose gel. The agarose gel electrophoresis was carried out according to the method described by T. Maniatis et al. (Molecular Cloning, pp. 156–161, Cold Spring Habor Laboratory (1984)). The DNA band containing luciferase c-DNA was cut off and introduced into a dialysis tube. After 2 ml TE buffer was added to the tube, and the tube was sealed. By electroelution, the DNA was eluted from the gel to the buffer. The DNA solution was removed from the tube and extracted with an equal volume of phenol saturated with water. After this sample solution was stirred, the aqueous layer was recovered, and then DNA was recovered by ethanol precipitation in accordance with the conventional manner.

10 μg of the DNA fragment thus obtained was dissolved in 126 μl TE buffer. Following addition of 16 μl Med buffer and 64 units of Sau 3AI (produced by Takara Shuzo Co., Ltd.), the sample was digested at 37° C. for 2 hours, and the total amount of the products were electrophoresed in a 5% (W/V) polyacrylamide gel, whereby DNA fragments were separated. The polyacrylamide electrophoresis was effected according to the method as described by A. Maxam (Methods in Enzymology, 65: 506(1980)). 1 μg of the 190 bp Sau 3AI fragment containing the luciferase c-DNA was isolated as described above.

1 μg of the luciferase c-DNA was labeled with [α-$^{32}$P] dCTP (produced by Amersham) in accordance with the nick translation method. The nick translation was carried out using a kit produced by Takara Shuzo Co., Ltd. in accordance with the method described in J. Mol. Biol., 113: 237–251 (1977) and Molecular Cloning, 109–112, Cold Spring Habor Laboratory (1982) as recommended by the manufacturer's instructions.

(10) Screening of Large Luciferase c-DNA (Colony Hybridization)

By use, as a probe, of the $^{32}$P-labelled luciferase c-DNA fragment as prepared above, the c-DNA library of the *Photinus pyralis* tail, in which the recombinant plasmid DNA pUC19 is a vector, was screened with in accordance with the colony hybridization method (Protein, Nucleic Acid, Enzyme (Japan), 26: 575–579 (1981)), whereby colonies containing luciferase c-DNA were obtained. A recombinant plasmid DNA contained in one of the colonies was names pALf3, and a plasmid DNA was prepared according to the method as described in (5) above. The *E. coli* carrying said recombinant plasmid DNA was named *E. coli* DH1 (pALf3). Said transformant *E. coli* has been deposited as ATCC 67462.

Figure 1:
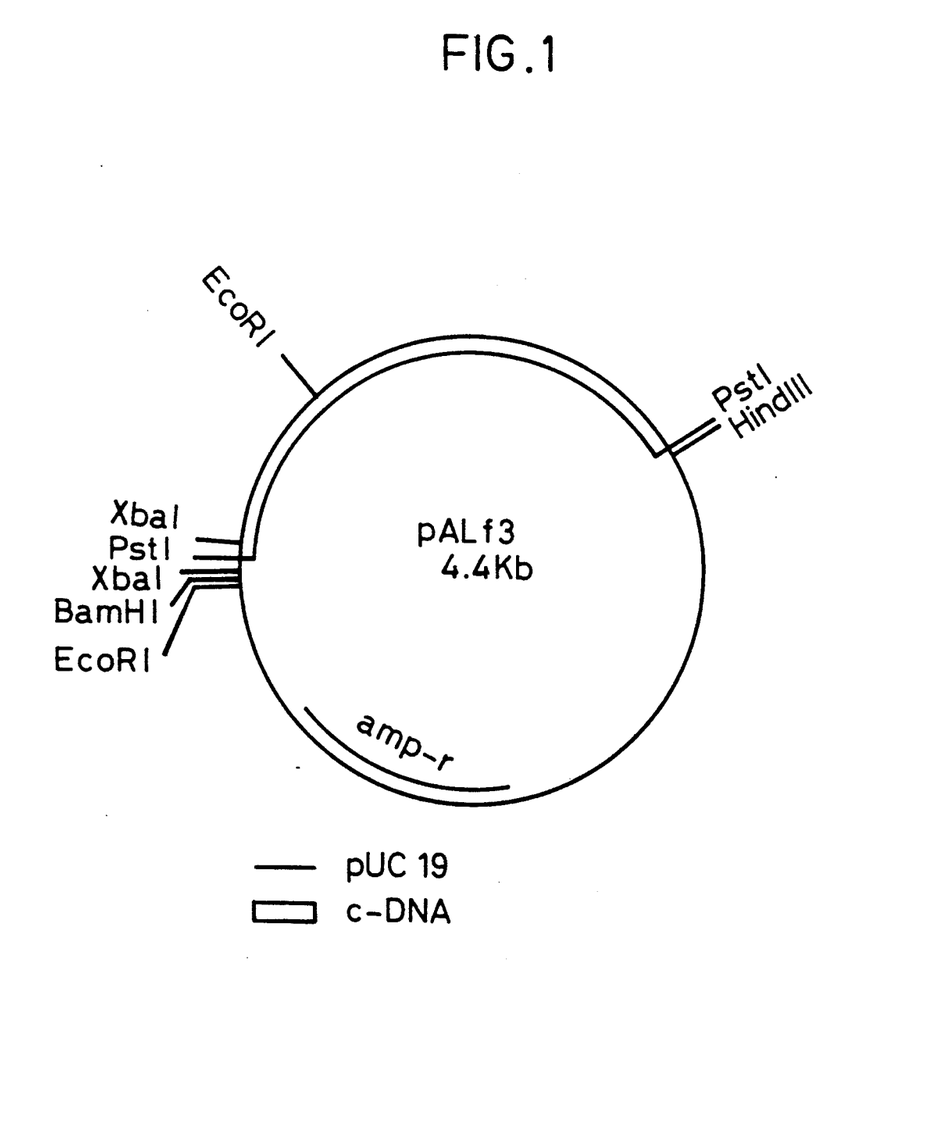
FIG. 1 shows cleavage map of recombinant plasmid DNA pALf with restriction enzymes.

The above recombinant plasmid DNA pALf3 was digested with one or two enzymes from the group consisting of Xba I, Hind III, Bam HI, Eco RI and Pst I (which all are produced by Takara Shuzo Co., Ltd.). The obtained DNA fragments were analyzed for mobility pattern by agarose gel electrophoresis, and the resulting patterns were compared with the standard mobility pattern of DNA fragments prepared by digesting a molecular weight marker, λ-DNA (produced by Takara Shuzo Co., Ltd.) with Hind III. The molecular weight of the luciferase cDNA fragment thus determined was 1,700 bp. The restriction enzyme map of the above plasmid is as set forth in FIG. 1.

(11) Preparation of m-RNA of *Luciola cruciata*

10 g of alive fireflies, *Luciola cruciata* (purchased from K.K. Seibu Department Store) were frozen in a supercryogenic temperature refrigerator, and the tails of fireflies were cut off by means of scissors. 18 ml of a guanidine isocyanate solution was added to 2 g of the tails thus obtained, and 1.1 mg of RNA were prepared according to 2 g of the tails thus obtained, above. 1.1 mg of the RNA were applied to oligo(dT)-cellulose column chromatography in accordance with the method as described in (1) above, whereby 30 μg of m-RNA of the *Luciola cruciata* tail were prepared.

(12) Construction of the c-DNA Library of *Luciola cruciata* Tail

Synthesis of c-DNA was carried out according to the method (Mol. Cell Biol., 2: 161 (1982) and Gene, 25: 263 (1983)) as recommended by the manufacturer's (Amersham) instructions. 0.9 μg double-stranded c-DNA was prepared from 2 μg RNA of *Luciola cruciata* tails. A polydeoxycytidine tail was attached to 0.3 μg of the c-DNA according to the method as described in (4) above.

According to the method as described in (7) above, 20 ng of the c-DNA were annealed to 500 ng of the plasmid DNA pUC19 with a polyguanosine tail attached at the Pst I site as prepared in (6) above. The resulting DNA was transformed into *E. coli* strain DH1 (ATCC 33849) according to the method as described by Hana-han (DNA Cloning, 1: 109–135 (1985)), so that the c-DNA of *Luciola cruciata* tail was prepared.

(13) Screening of Luciferase c-DNA Derived from *Luciola cruciata*

10 μg of the transformant plasmid DNA pALf3 obtained in (10) above were dissolved in 90 μl TE buffer. Following addition 25 units of restriction enzyme Eco RI and 25 units of restriction enzyme Cla I (which are produced by Takara Shuzo Co., Ltd.), the DNA was cleaved at 37° C. for 2 hours. The 800 bp Eco RI/Cla I DNA fragment containing luciferase c-DNA derived from *Photinus pyralis* (American firefly) was isolated from the cleaved recombinant plasmid DNA pALf3 according to the method of agarose gel electrophoresis as described (9) above, whereby 1 μg of Eco RI/Cla I DNA fragment was obtained. 1 μg of the DNA was labeled with [α-$^{32}$P] dCTP (produced by Amarsham) in accordance with the nick translation method as described in (9) above. By use as a probe of $^{32}$P-labelled Eco RI/Cla I DNA fragment, E. coli carrying Luciferase c-DNA derived from Luciola cruciata was selected by screening the c-DNA library of the Luciola cruciata tail in accordance with the colony hybridization method as described in (10) above. As a result, seveal E. coli colonies hybridized with the probe were obtained. Recombinant plasmid DNA contained in one of the colonies was named pGLf 1, and the recombinant plasmid DNA was isolated according to the method as described in (5) above. The E. coli carrying said recombinant plasmid DNA was named E. coli DH1 (pGLf1). Said transformant strain has been deposited as ATCC 67582.

Figure 2:
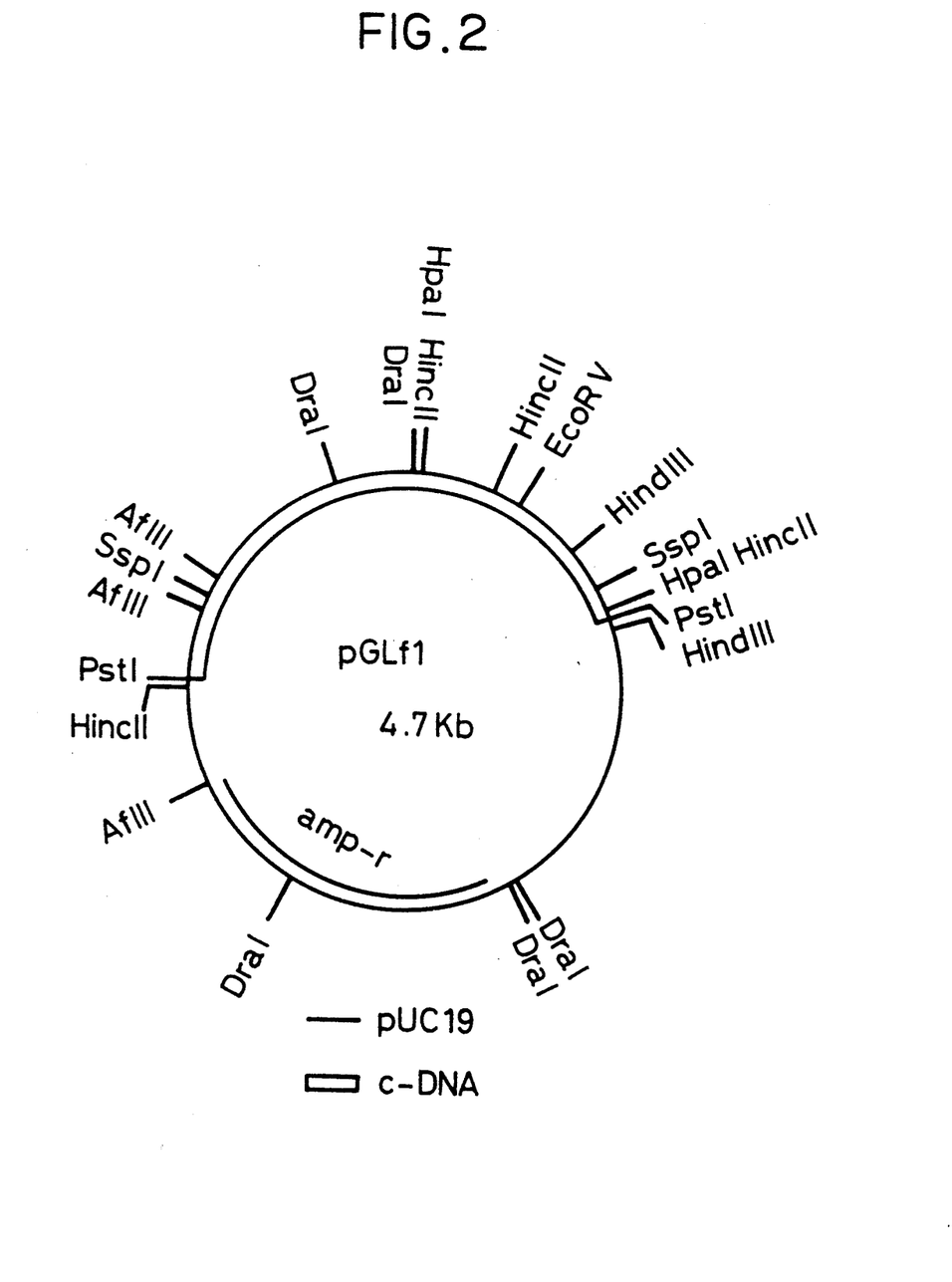
FIG. 2 shows cleavage map of recombinant plasmid DNA pGLf with restriction enzymes.

The recombinant plasmid DNA pGLf 1 was digested with one or two enzymes from the group consisting of Hpa I, Hind III, Eco RV, Dra I, Afl II, Hinc II, and Pst I (all of which are produced by Takara Shuzo Co., Ltd.) and Ssp I (produced by New England Bio-Lab). The obtained DNA fragments were analyzed for mobility pattern by agarose gel electrophoresis, and the resulting pattern was compared with the standard mobility pattern of DNA fragments having been prepared by digesting a molecular weight marker, λ-phage DNA (produced by Takara Shuzo Co., Ltd.) with Hind III. As a result, the molecular weight thus determined was 2,000 bp. The restriction enzyme map of the above plasmid is as set forth in FIG. 2.

(14) Analysis of Base Sequence of Luciferase c-DNA Derived from Luciola cruciata 10 μg of the recombinant plasmid DNA pGLf 1 were digested with restriction enzyme Pst I (produced by Takara Shuzo Co., Ltd.), whereby 2.5 μg of 2.0 kb DNA fragment containing the luciferase c-DNA were obtained. The DNA fragment was inserted into the Pst I site of plasmid DNA pUC 119 (produced by Takara Shuzo Co., Ltd.), and the resulting plasmid DNAs were named pGLf 2 and pGLf 3 depending on the orientation of the inserted c-DNA. Cleavage with Pst I of recombinant plasmid DNA pGLf 1 and plasmid DNA pUC 119 (the method as described in (6) above), isolation of the luciferase c-DNA fragment by agarose gel electrophoresis (the method as described in (9) above), ligation of plasmid DNA pUC 119 with the luciferase c-DNA fragment (the method as described in (5) above), transformation of E. coli strain JM101 (ATCC 33876) with the construct (the method as described in (5) above), and preparation of recombinant plasmid DNAs pGLf 2 and pGLf 3 (the method as described in (5) above) were carried out as described before.

Then, plasmid DNAs with a variety of deletions introduced into luciferase c-DNA were prepared from recombinant plasmid DNAs pGLf 2 and pGLf 3 using a deletion kit for kilosequence (produced by Takara Shuzo Co., Ltd.) according to the method as described by Heinkoff [Gene, 28: 351-359 (1984)]). These plasmid DNAs were introduced into E. coli strain JM 101 (ATCC 33876) according to the method as described in (5) above. The E. coli thus obtained was infected with helper phage M13K07 (manufactured by Takara Shuzo co., Ltd.), to prepare single-stranded DNA according to the method as described by Messing [Methods in Enzymology, 101: 20 to 78 (1983)]. The sequencing by the obtained single-stranded DNA using an M13 sequencing kit (manufactured by Takara Shuzo Co., Ltd.) was carried out in accordance with the Messing method (see above). Gel electrophoresis for the analysis of base sequence was carried out in 8% (W/V) polyacrylamide gel (manufactured by Fuji Film Co., Ltd.).

The whole base sequence of only the luciferase c-DNA derived from Luciola cruciata and the amino acid sequence deduced form the c-DNA are set forth in Sequence ID No. 1 and Sequence ID No. 2, respectively.

(15) Construction of Recombinant Plasmid DNA pGLf 37

First, an explanation is given to the preparation of the DNA fragment comprising vector DNA and the luciferase gene (from which the base sequence encoding 9 amino acids from the N-terminal has been deleted) originating in Luciola cruciata, 1 μg of recombinant plasmid DNA pGLf 1 was dissolved in 90 μl water, followed by addition of 10 μl Med buffer and 20 units of Pst I (produced by Takara Shuzo Co., Ltd.), and the mixture was digested at 37° C. for 2 hours. To the sample solution thus digested was added an equal volume of water-saturated phenol, and the sample was precipitated with ethanol in accordance with the conventional manner. According to the method as described in (5) above, the thus obtained precipitates were ligated and transformed into E. coli JM 101 (ATCC 33876).

According to the method as described in (5) above, DNA was isolated from the resulting transformant. The DNA was digested with one or two enzymes from the group consisting of restriction enzymes Ssp I, Eco RV, and Pst I, and the recombinant plasmid which is opposite to the original recombinant plasmid pGLf 1 in respect of the orientation of the c-DNA was selected, and it was named pGLf 10.

10 μg of the recombinant plasmid DNA pGLf 10 were dissolved in 90 μl water. After 10 μl Med buffer and 10 units of Ssp I (produced by New England Bio-Lab) were added to the solution, the mixture wad incubated at 37° C. over 30 min., whereby partially digested products were obtained. From the products, there were isolated 2 μg of 4.0 kb DNA fragment comprising most of the vector DNA and the luciferase gene lacking the base sequence encoding 9 amino acids from the N-terminal.

Subsequently, 1 μg of the DNA fragment was dissolved in 95 μl water. Following addition of 5 μl of 1M Tris-HCl buffer (pH 8.0) and 1 μl (0.3 unit) of alkali phosphatase (produced by Takara Shuzo Co., Ltd.), the mixture was incubated at 65° C. for 1 hour and was then subjected to protein removal treatment and ethanol precipitation in accordance with the conventional manner, and then 1 μl of 4.0 kb DNA fragment dephosphorylated at both ends was obtained.

10 μg of plasmid DNA pKN 206 [which is disclosed in Agric. Biol. Chem., 50: 271-279 (1986)] were dissolved in 90 μl water. After 10 μl Med buffer and 20 units of Cla I (produced by Takara Shuzo Co., Ltd.) were added to the solution, the mixture was incubated at a temperature of 37° C. for 2 hours, so that completely digested sample was obtained. 10 units of Ssp I as stated were added to the sample, followed by incubation at a temperature of 37° C. for 30 min., whereby products partially digested with Ssp I were obtained. Then, the products were subjected to protein removal treatment (by phenol extraction) and ethanol precipitation in accordance with the conventional manner. The precipitates obtained were dissolved in 100 µl TE buffer, and 500 b DNA fragment containing almost all the trp promoter was isolated according to the manner as described in (9) above.

Next, the preparation of synthetic DNA is explained.

The luciferase gene contained in said 4.0 kb DNA fragment, on the basis of the base sequence, lacked in a nucleotide sequence encoding 9 amino acids from the N-terminal.

The trp promoter contained in the above 500 b DNA fragment lacked in a part of the sequence between the SD and the ATG. In order to fill the sequence encoding 9 amino acids from the N-terminal of luciferase and the sequence between the SD and the ATG of trp promoter, the following two types of synthetic DNAs (Sequences ID Nos. 3 and SEQ ID NO. 4) were synthesized using a System 1 Plus DNA synthesizer manufactured by Beckman.

From each of the two types of synthetic DNAs, 20 µg of purified synthetic DNA was prepared using NENSORB PREP manufactured by DuPont. 1 µg each of the purified synthetic DNA was dissolved in 45 µl water, followed by addition of 5 µl of an 10× kination buffer [0.5M Tris-HCl buffer (pH 7.6), 0.1M $MgCl_2$, 50 mM dithiothreitol, and 10 mM ATP] and 10 units (1 µl) of T4 polynucleotide kinase (produced by Takara Shuzo Co., Ltd.). Subsequently, the sample was incubated at a temperature of 37° C. for 1 hour and then subjected to protein removal treatment (by phenol extraction) and ethanol precipitation in accordance with the conventional manner, and 1 µg of each of the two types of synthetic DNAs with 5' end phosphorylated was obtained. Then, ligation reaction was made for the preparation of the objective plasmid DNA. 1 µg of the above dephosphorylated 4.0 Kb DNA fragment containing the luciferase gene (from which the base sequence encoding 9 amino acids from the N-terminal has been deleted) and vector DNA, 1 µg of the above 500 b DNA fragment containing the trp promoter, and 0.1 µg of each of the two types of synthetic phosphorylated DNA were dissolved in 8 µl water. Following addition of 1 µl of an 10× ligation buffer [200 mM $MgCl_2$, 660 mM Tris-HCl buffer (pH 7.6), 10 mM ATPP, and 150 mM dithiothreitol] and 1 unit (1 µl) of T4DNA ligase (produced by Takara Shuzo Co., Ltd.), the mixture solution was allowed to react over 16 hours at a temperature of 16° C. According to the method as described in (5) above, the reacted solution was transformed into E. coli JM101 (ATCC 33876) and, according to the method as described in (5) above, plasmid DNA was isolated from the resulting transformant and then digested with one or two enzymes from the group consisting of restriction enzymes Ssp I, Eco RV, and Pst I. The digested products were developed by electrophoresis in a 0.7% agarose gel, so that the plasmid containing the trp promoter and the luciferase cDNA was obtained, and this recombinant plasmid was named pGLf 37. The E. coli carrying said plasmid was named E. coli JM101 pGLf 37).

(16) Mutagenesis of Recombinant Plasmid DNA pGLf37

30 µg of the recombinant plasmid DNA pGLf37 were dissolved in 100 µl of a hydroxylamine solution [0.8M hydroxylamine chloride, 0.1M phosphate buffer (pH 6.0), and 1 mM EDTA] and then subjected to mutation treatment at 65° C. for 2 hours. After incubation, DNA was precipitated with ethanol in a conventional way, thereby giving precipitates. The precipitates recovered were dissolved in TE buffer [10 mM Tris-HCl buffer (pH 7.5) and 1 mM EDTA] and transformed into E. coli strain JM101 (ATCC 33876) according to the Hana-han method [DNA Cloning; 1: 109–135.(1985)]. Then, said microorganism was inoculated into an LB-amp agar medium [1% (W/V) bactotrypton, 0.5% (W/V) yeast extract, 0.5% (W/V) NaCl, (50 µg/ml) ampicillin, and 1.4% (W/V) agar)], followed by incubation at 37° C. Colonies came to appear after 12 hours' incubation, and they were incubated for further 18 hours under shaking at 37° C. in 3 ml LB-amp medium [1% (W/V) bactotrypton, 0.5% (W/V) yeast extract, 0.5% (W/V) NaCl, and (50 µg/ml) ampicillin]. 0.5 ml of the culture liquid was inoculated into 10 ml of an LB-amp medium of the same composition as described above, followed by incubation at 37° C. for 4 hours under shaking. Subsequently, each of the culture liquids was centrifuged at 8,000 r.p.m. for 10 min., whereby 20 mg of wet bacteria bodies were obtained from each culture liquid.

The recovered bacteria were suspended in 0.9 ml of a buffer consisting of 0.1M $KH_2PO_4$ (pH 7.8), 2 mM EDTA, 1 mM dithiothreitol, and 0.2 mg/ml protamine sulfate, followed by addition of 100 µl of 10 mg/ml lysozyme solution, and the suspension was placed on ice for 15 min. Then, this suspension was frozen in methanol on dry ice, and was then allowed to stand at a temperature of 25° C., thereby melting completely. This solution was centrifuged at 12,000 r.p.m. for 5 min., whereby 1 ml crude enzyme was obtained as supernatant.

The resulting crude enzyme solution containing luciferase was heated at 50° C. for 10 min., and 10 µl of the crude enzyme was examined for titer in accordance with the method as disclosed in Japanese Patent Appln. LOP Publication No. 141,592/1989. As a result, it was found that the firefly luciferase thus obtained is superior in thermostability to the wild-type luciferase of GENJI firefly.

The crude enzyme solution was further purified according to the method as disclosed in Japanese Patent Appln. LOP Publication No. 141,592/1989 and then heated in the same way as above. The enzyme thus purified was examined for titer, and the result indicated that this enzyme is superior in thermostability to the purified wild-type luciferase. The thus obtained recombinant plasmid DNA into which the gene encoding thermostable luciferase is inserted was named pGLf37T-M-2. The E. coli strain JM 101 (pGLf37T-M-2), i.e. E. coli transformed with said recombinant plasmid DNA, has been deposited as the accession No. FERM BP-3452 with Fermentation Research Institute, the Agency of Industrial Science of Technology.

In the mutant firefly luciferase thus obtained, threonine at the 217-position of the amino acid sequence of the wild-type firefly luciferase is replaced by isoleucine. 100 µl of an enzyme solution containing 100 Kcount of the present purified enzyme [10 mM phosphate buffer (pH 7.6) containing 10% saturated ammonium sulfate, 0.2 mM disodium ethylenediaminetetra acetate, and 0.2% (W/V) albumin] was examined for residual enzyme activity after kept at a temperature of 50° C. for 60 min. As a result, it was found that the present enzyme keeps 65% of residual enzyme activity under the above conditions.

As a control, the wild-type firefly luciferase was examined for residual enzyme activity in the same way as described above. However, no activity could be found in this enzyme.

(17) Site-specific Mutagenesis

Next, a method for replacement of threonine, i.e. the amino acid at the 217-position of the amino acid sequence of luciferase of GENJI firefly, by a hydrophobic amino acid valine or leucine is described.

10 μg of recombinant plasmid DNA pGLf 37 were digested with two restriction enzymes Eco RI and Pst I (which are produced from Takara Shuzo Co., Ltd.), whereby 2.5 μg of 2.1 kb DNA fragment containing the luciferase c-DNA were obtained. The DNA fragment was subcloned in plasmid DNA pUC119 (produced by Takara Shuzo Co., Ltd.), and the plasmid DNA thus obtained was named pGPM-1. Then, the recombinant plasmid pGPM-1 was introduced into E. coli JM101 (ATCC 33876), according to the method as described in (5) above.

The E. coli thus obtained was infected with helper phage M13K07 (manufactured by Takara Shuzo Co., Ltd.), and single-stranded DNA was prepared according to the method as described by Messing [Methods in Enzymology, 101: 20–78 (1983)]. Site-specific mutagenesis by the resulting single-stranded DNA was effected using In Vitro Mutagenesis System Version 2.0 (manufactured by Amersham). As primers for site-specific mutagenesis, the following two types of synthetic DNAs were synthesized according to the method as described in (15) above. That is, the synthetic DNA indicated as a primer for valine in Sequence ID No. 5 and the synthetic DNA indicated as a primer for leucine in Sequence ID No. 6 were used as primers for site-specific mutagenesis, respectively.

The sequencing of the site-specifically mutagenized genes were carried out using a Dye-Primer Taq Sequencing kit (manufactured by Applied Biosystems, Inc.), and their electrophoresis and analysis was carried out using an Ab1373A DNA sequencer (manufactured by Applied Biosystems, Inc.). The site-specifically mutagenated genes thus obtained encode the amino acid sequences in which the amino acid at the 217-position of wild-type firefly luciferase is replaced by valine or leucine, and the former gene was named pGPM-1-Val and the latter pGMP-1-Leu.

Then, 10 μg each of the site-specifically mutagenated genes pGPM-1-Val DNA and pGPM-1-Leu DNA were digested with two restriction enzymes Eco RI and Pst I (which are produced by takara Shuzo Co., Ltd.), whereby 2.5 μg each of 2.1 kb DNA fragment containing the luciferase c-DNA were obtained. Each of the DNA fragment was inserted into luciferase-CDNA-free region of a vector obtained by digestion of recombinant plasmid DNA pGLf37 with two restriction enzymes Eco RI and Pst I (which are produced by Takara Shuzo Co., Ltd.), and the plasmid DNAs thus cloned were named pGLf37-217Val and pGLf37-217Leu, respectively.

Then, the recombinant plasmids pGLf37-217Val and pGLf37-217Leu were introduced into E. coli strain JM101 (ATCC 33876), according to the method as described in (5)above, whereby transformants E. coli JM101 pGLf37-217Val and E. coli JM101 pGLf37-217Leu were obtained. The E. coli JM101 pGLf37-217Val has been deposited as FERM BP-3647 and the E. coli JM101 pGLf37-217Leu as FERM BP-3648 with Fermentation Research Institute, Agency of Industry Science and Technology. A crude enzyme solution was obtained from the transformant, according to the method as described in (16) above, and the enzyme was purified according to the method as disclosed in Japanese Patent Appln. LOP Publication No. 141,592/1989. The purified luciferase thus obtained was heated at 50° C. for 60 min., and 10 μl of the enzyme thus treated was measured for residual enzyme activity, according to the method as disclosed in japanese Patent Appln. LOP Publication No. 141,592/1989. As a result, it was found that the luciferase derived from E. coli JM101 pGLf37-217Val keeps 65% of residual enzyme activity, and the luciferase derived form E. coli JM101 pGLf37-217Leu keeps 70% of residual enzyme activity.

Next, a description is provided for a method for the replacement of alanine at the 217-position in the luciferase amino acid sequence of HEIKE firefly (Luciola lateralis) by the hydrophobic amino acid of valine, leucine, or isoleucine.

The recombinant plasmid pHLf7 obtained according to the method as disclosed in Japanese Patent Appln. LOP Publication No. 171,189/1990 was introduced into E. coli JM101 (ATCC 33876), according to the method as described in (5) above. The whole nucleotide sequence of only luciferase c-DNA derived from Luciola lateralis is shown in Sequence ID No. 7, and the amino acid sequence of the polypeptide deduced from the c-DNA is shown in Sequence ID No. 8. From the E. coli thus obtained, single-stranded DNA was prepared according to the method as described in (17) above. The site-specific mutagenesis by the resultant single-stranded DNA was effected using In Vitro Mutagenesis System Version-2.0 (manufactured by Amersham).

According to the method as described in (15) above, the following 3 types of synthetic DNAs were synthesized as primers for site-specific mutagenesis. That is, the synthetic DNA indicated as a primer for valine in Sequence ID No. 9, the synthetic DNA indicated as a primer for leucine in Sequence ID No. 10, and the synthetic DNA indicated as a primer for isoleucine in Sequence ID No. 11 were used as primers for site-specific mutagenesis, respectively.

The sequencing of the site-specifically mutagenated gene was carried out using a Dye-Primer Taq Sequencing kit (manufactured by Applied Biosystems, Inc.), and analytical electrophoresis was conducted using an ABI 373A DNA sequencer (manufactured by Applied Biosystems, Inc.). The thus obtained site-specifically mutagenated luciferase genes int he recombinant plasmids encode, in the corresponding gene region, that amino acid at the 217-position of wild-type HEIKE firefly luciferase which has been converted into valine, leucine, and isoleucine, and the recombinant plasmids with such genes were names pHLf7-217Val, pHLf7-217Leu, and pHLf7-217Ile, respectively.

Subsequently, the recombinant plasmids pHLf7-217Val, pHLf7-217Leu, and pHLf7-217Ile, respectively, were transformed into E. coli strain JM101 (ATCC 33876), whereby E. coli JM101 pHLf7-217Val, E. coli JM101 pHLf7-217Leu, and E. coli JM101 pHLf7-217Ile were obtained. The transformants E. coli JM101 pHLf7-217Val, E. coli JM101 pHLf7-217Leu, and E. coli JM101 pHLf7-217Ile were deposited as Accession Nos. FERM BP-3839, FERM BP-3841, and FERM BP-3840, respectively, with Fermentation Research Institute, the Agency of Industrial Science of Technology. According to the method as described in (16)

above, a crude enzyme solution was obtained from each transformant, and it was further purified according to the method as disclosed in Japanese Patent Appln. LOP Publication No. 262,791/1989. The purified luciferase thus obtained was heated at 50° C. for 60 min., and 10 μl of the solution was measured for residual enzyme activity in accordance with the method as disclosed in Japanese Patent Appln. LOP Publication No. 262,791/1989. As a result, it was found that 65% or more of residual enzyme is kept in every case.

As is evident from the above illustration, the luciferase of the invention was found to be extremely superior in thermostability to the control luciferase.

EFFECT OF THE INVENTION

The present invention provides a gene of thermostable luciferase of firefly, recombinant DNA containing said gene, and a process for the preparation of thermostable luciferase of firefly by a microorganism carrying said recombinant DNA, as well as novel thermostable luciferase of firefly thus obtained. According to the present method, thermostable luciferase of firefly can be efficiently produced, so that the present invention is extremely useful in industry.

---

What is claimed is:

1. A gene encoding a thermostable luciferase of firefly, which encodes the amino acid sequence of the wild-type firefly luciferase of *Luciola cruciata* (Genji firefly, Seq. ID No. 2) or *Luciola lateralis* (Heike firefly, Seq. ID No. 8), in which the amino acid at the 217-position is replaced by a hydrophobic amino acid.

2. A gene encoding a thermostable luciferase of firefly according to claim 1, wherein the hydrophobic amino acid is isoleucine, leucine, or valine.

3. Recombinant DNA, which comprises the gene encoding a thermostable luciferase of firefly according to claim 1 inserted into vector DNA.

4. Process for the preparation of a thermostable luciferase of firefly, which comprises incubation in a culture medium of a microorganism belonging to the genus Escherichia, carrying the recombinant DNA according to claim 3 and being capable of producing thermostable luciferase of firefly, and subsequent collection of thermostable luciferase of firefly from said culture medium.

5. A thermostable luciferase of firefly, wherein an amino acid at the 217-position of the amino acid sequence of wild-type firefly luciferase of *Luciola cruciata* (GENJI SEQ. ID No. 2firefly) or *Luciola lateralis* (HEIKE firefly SEQ. ID. No. 8) is replaced by a hydrophobic amino acid.

* * * * *